US008823500B2

(12) United States Patent
Heath et al.

(10) Patent No.: US 8,823,500 B2
(45) Date of Patent: *Sep. 2, 2014

(54) SYSTEM AND METHOD FOR AUTOMATING AND VERIFYING PRODUCT VALUE, USAGE, AND SUITABILITY FOR USE OR SALE

(75) Inventors: Chester Heath, Boca Raton, FL (US); Pedro Martinez, Boca Raton, FL (US)

(73) Assignee: The Quantum Group, Inc., Lake Worth, FL (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/302,557

(22) Filed: Nov. 22, 2011

(65) Prior Publication Data

US 2012/0125994 A1 May 24, 2012

Related U.S. Application Data

(63) Continuation-in-part of application No. 12/470,550, filed on May 22, 2009, now Pat. No. 8,154,390.

(51) Int. Cl.
*G08B 1/00* (2006.01)
(52) U.S. Cl.
USPC .............................. 340/309.16; 340/539.12
(58) Field of Classification Search
USPC ............... 340/309.16, 539.12, 573.1, 309.7; 368/10; 705/2
See application file for complete search history.

(56) References Cited

U.S. PATENT DOCUMENTS

| 4,617,557 | A | 10/1986 | Gordon |
| 5,412,372 | A | 5/1995 | Parkhurst et al. |
| 5,441,047 | A | 8/1995 | David et al. |
| 5,842,978 | A | 12/1998 | Levy |
| 5,937,387 | A | 8/1999 | Summerell et al. |
| 5,963,136 | A | 10/1999 | O'Brian |
| 6,221,010 | B1 | 4/2001 | Lucas |
| 6,380,858 | B1 | 4/2002 | Yarin et al. |
| 6,562,001 | B2 | 5/2003 | Lebel et al. |
| 6,670,885 | B2 | 12/2003 | Kosaka |
| 6,973,371 | B1 | 12/2005 | Benouali |
| 7,230,521 | B2 | 6/2007 | Terenna |
| 7,366,675 | B1 | 4/2008 | Walker et al. |
| 7,755,478 | B2 | 7/2010 | Niemiec et al. |
| 7,928,835 | B1 | 4/2011 | Jovanov et al. |
| 7,956,727 | B2 | 6/2011 | Loncar |
| 8,154,390 | B2 * | 4/2012 | Heath et al. .............. 340/309.16 |

(Continued)

OTHER PUBLICATIONS

International Search Report and the Written Opinion of the ISA issued in International Application No. PCT/US2012/52404 on Nov. 6, 2012. (14 pages).

(Continued)

*Primary Examiner* — John A Tweel, Jr.
(74) *Attorney, Agent, or Firm* — Novak Druce Connolly Bove + Quigg LLP

(57) ABSTRACT

A computer-based system for monitoring product usage, value, and suitability for use or sale. The system can include one or more processors configured to process and manage data. Additionally, the system can also include product packaging comprising a machine-readable medium. Notably, the machine-readable medium can comprise product information among other types of information. The one or more processors can be configured for receiving the product information of the machine-readable medium. The machine-readable medium and corresponding medication information can be adjusted based on automated signals or interactive signals, where the signals are generated based on current or historical data regarding the product or the packaging.

24 Claims, 9 Drawing Sheets

(56) References Cited

U.S. PATENT DOCUMENTS

| | | |
|---|---|---|
| 2006/0111944 A1 | 5/2006 | Sirmans et al. |
| 2008/0098313 A1 | 4/2008 | Pollack |
| 2008/0102856 A1 | 5/2008 | Fortescue et al. |
| 2008/0188261 A1 | 8/2008 | Arnone et al. |
| 2008/0215623 A1 | 9/2008 | Ramer et al. |
| 2009/0215469 A1 | 8/2009 | Fisher et al. |

OTHER PUBLICATIONS

Mehrotra et al., "Elements of artificial neural networks," MIT Press (1997).

Non Final Office Action mailed on Dec. 15, 2011 in U.S. Appl. No. 12/349,714. (25 pages).

Non Final Office Action mailed on Jul. 15, 2011 in U.S. Appl. No. 12/470,550. (13 pages).

\* cited by examiner

502

504

SYSTEM AND METHOD FOR AUTOMATING AND VERIFYING PRODUCT VALUE, USAGE, AND SUITABILITY FOR USE OR SALE

CROSS-REFERENCE TO RELATED APPLICATIONS

This application claims the benefit of U.S. patent application Ser. No. 12/470,550, entitled "SYSTEM AND METHOD FOR AUTOMATING AND VERIFYING MEDICATION COMPLIANCE", filed May 22, 2009, which is herein incorporated by reference in its entirety.

FIELD OF THE INVENTION

The present invention is related to the fields of packaging and point of sale pricing, and more particularly, to computer-based systems and methods for automatically determining and verifying product value, usage, and suitability for sale or use.

BACKGROUND OF THE INVENTION

Advances in patient care have helped to dramatically increase patients' lifespan and quality of life through the development of more effective treatments, medications, and medical technologies. Despite these advances, a leading cause of medical patient fatalities is accidental patient non-compliance with pharmaceutical dosage programs. For example, many patients often forget to take their medications, take too many doses of their medications, take the wrong medications, or take their medications in an incorrect manner. Additionally, some patients even forget to fill their prescriptions in the first place. As a result, taking medications in a non-compliant fashion often leads to a prolonging of disease-related symptoms, an increase in serious complications, unnecessary additional medical visits, higher medical costs, and possibly even death.

People often use the assistance of calendars, physicians, other people, their own memory, and other methods to help remind them to take a particular medication or to help verify that they took the medication according to the proper regimen. However, such methods often fail to adequately remind the patient to take their medications on a regular basis or in an effective manner. Such methods further fail to verify that the patient actually took the medication appropriately.

Additionally, it is generally difficult to determine the state of medications. For example, in the case of medications that need to be stored at specific temperatures, it is difficult to determine whether or not the required storage conditions for the medication have been maintained throughout the storage life of the product.

The issues described above are generally not limited to the field of medications. Commoditization of products, both medical and non-medical, has lead to the extensive use of pre-packaging of products. However, current labeling techniques generally make it difficult for users to ascertain the state of the product, especially in the case of perishable goods. For example, although perishable goods (e.g., frozen goods) may include an expiration date, this date is generally based on specific storage conditions (e.g., the goods were continually stored in a freezer). As a result, buyers of such perishable goods must assume that the sellers have followed proper storage practices for the goods, which may or may not be accurate.

Similar issues arise with respect to determining the extent to which prepackaged goods have been used and whether any other events have occurred that have affected the quality and thus the value of the goods.

SUMMARY OF THE INVENTION

The present invention is directed to systems and methods for packaging. In particular, computer-based systems and methods are provided for monitoring product usage, value, and suitability for use or sale. The system can include one or more processors configured to process and manage data. Additionally, the system can also include a product packaging comprising a machine-readable medium. Notably, the machine-readable medium can comprise product information among other types of information. The one or more processors can be configured to receive the product information of the machine-readable medium. The machine-readable medium and corresponding product information can be adjusted based on automated signals or interactive signals, where these signals are generated based on current or historical data regarding the product or the packaging.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
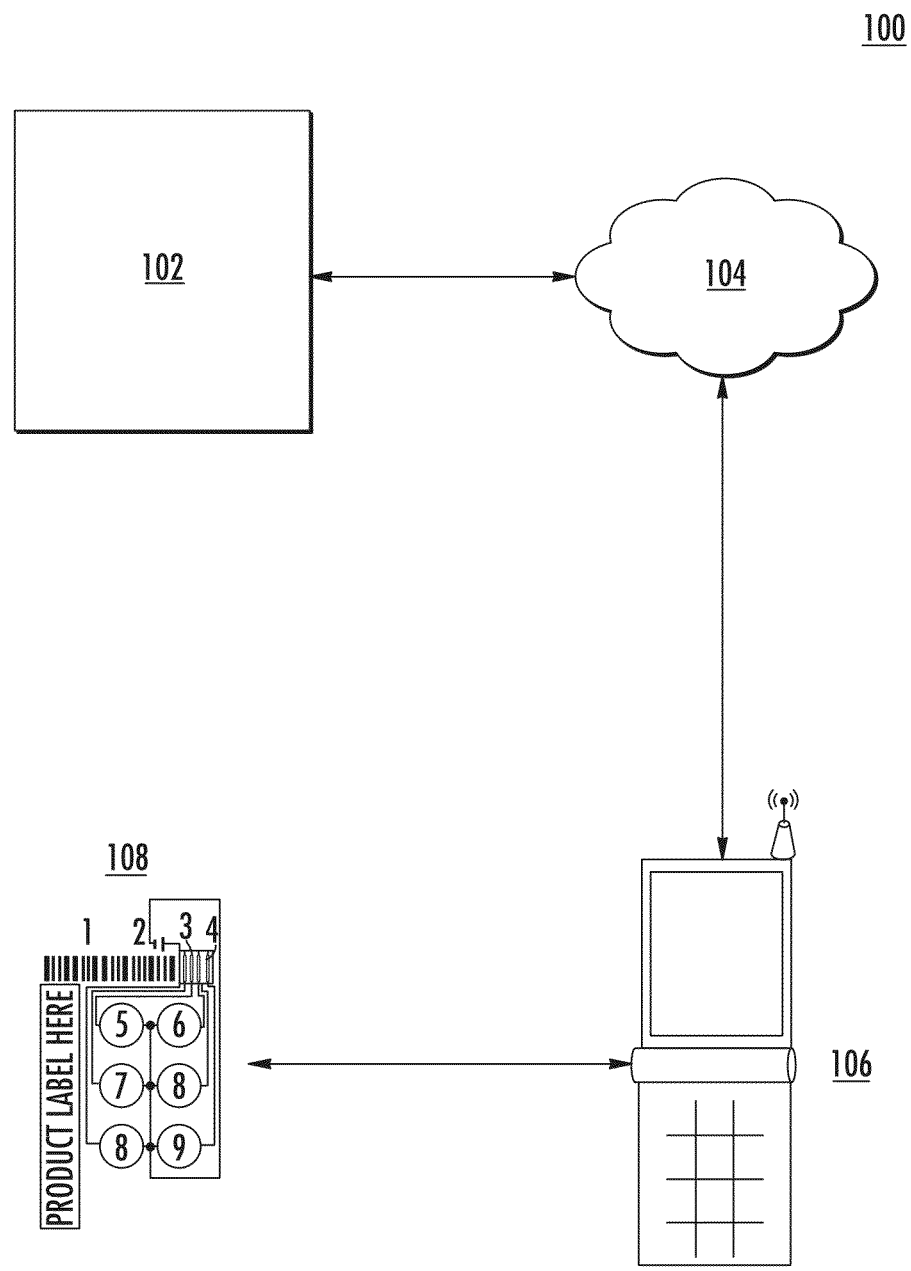
FIG. 1 is a schematic view of a system for monitoring medication compliance, according to one embodiment of the invention.

Various embodiments of the invention are discussed in detail below. While specific implementations are discussed, it should be understood that this is done for illustration purposes only. A person skilled in the relevant art will recognize that other components and configurations may be used without parting from the spirit and scope of the invention.

The various embodiments are directed to systems and methods for packaging that automate the process of determining a value, usage, and suitability for use or sale of packaged products. In particular, the various embodiments provide packaging that includes labels that can be used not only to identify the products therein, but also packaging that is configured, based on the occurrence of an event or a condition, to alter the labels to indicate value, usage, and suitability for use or sale. In the various embodiments, the labels can be human-readable, machine-readable, or a combination of both. A "human-readable" label, as used herein, refers to a label in which information stored therein can be discerned without the aid of a machine or computing device. A "machine-readable" label, as used herein, refers to a label in which information stored therein can be discerned solely only with the aid of a machine or a computing device.

In the various embodiments, the labels can be configured to operate in an automated or interactive manner. An automated manner of operation refers to operating without external control. For example, the label can include a sensor that changes automatically to changes in temperature (via a temperature sensor), agitation or shaking (via a pressure sensor or the like), tampering, opening, or removal of products (via a tampering sensor), or other events and conditions for the product of the packaging. On the other hand, an interactive manner of operation refers to operating only in the presence of external control. For example, the label can be configured to changes in response to radio frequency signals generated by a user or any other external control signal provided by a user.

Further, the labels in the various embodiments can be configured to indicate current or historical data. A label configured to indicate current data simply changes in real time or spontaneously as conditions change or events occur. An example of such a label would be a label that changes in response to changes in the current temperature. A label configured to indicate historical data would one that changes after an event occurs or some other condition is satisfied. An example of such a label would be one that changes when a temperature threshold is met or if shaking, agitation, or tampering has occurred in the past.

In the various embodiments, the labels disclosed herein can be implemented in any combination. That is, labels in accordance with the various embodiments can include portions implemented to provide (1) automated operation/current data; (2) automated operation/historical data; (3) interactive operation/current data; and (4) interactive operation/historical data.

Having described some of the main aspects of the invention, various exemplary embodiments are described below. Although the various embodiments will be described primarily with respect to medication packaging, the exemplary embodiments described below are provided solely for illustrative purposes and should not be considered limiting in any way.

Referring initially to FIG. 1, a system 100 for monitoring medication compliance, according to one embodiment of the invention, is schematically illustrated. The system can include a processor 102 configured to process and manage data. The system 100 can also include a communications network 104 and a communications device 106. The communications device 106 can be a personal digital assistant (PDA), cellular telephone, land-line phone, mobile device, computer, or other device. Notably, the communications device 106 can be communicatively linked to the processor 102 via the communications network 104 or otherwise. Additionally, the system 100 can include a medication packaging 108. The medication packaging 108 can include, but is not limited to including, a machine-readable medium, wherein the machine-readable medium can comprise medication information or other types of information.

The machine-readable medium can be a barcode, optical disk, magnetic disk, readable card, readable tape, magnetic strip, radio frequency tag, or other machine-readable medium. Also, the medication information included in the machine-readable medium can describe, but is not limited to describing, the medication included in the medication packaging 108 in a manner that is consistent with the labeling on the package itself. Even though one processor 102, one communications network 104, one communications device 106, and one medication packaging 108 are shown, it will be apparent to one of ordinary skill based on the description that a greater number of processors, communications networks, communications devices, and medication packaging can be used according to the invention.

Notably, the processor 102 can be implemented in hardwired, dedicated circuitry for performing the operative functions described herein. In another embodiment, the processor 102 can be implemented in computer-readable code configured to execute on a particular computing machine. In yet another embodiment, however, the processor 102 can be implemented in a combination of hardwired circuitry and computer-readable code.

Operatively, the processor 102 can be configured to receive the medication information of the machine-readable medium and the processor 102 can store and process the medication information. Notably, the machine-readable medium and corresponding medication information can be adjustable based on a dispensing of a medication from the medication packaging 108. In a particular embodiment, the processor 102 can be configured to communicatively link to the communications device 106. The patient can be instructed by the communications device 106 and/or the processor 102 to take one or more medications associated with the medication packaging 108. For example, the processor 102 can place an automated call to the patient's cellular phone, wherein the call can include a reminder telling the patient to take a certain quantity of medication from the medication packaging 108.

The processor 102 and/or the communications device 106 can then be configured to determine a condition of the medication packaging 108. The condition of the medication packaging 108 can indicate, but is not limited to indicating, that a medication from the medication packaging has been dispensed, that the medication and/or medication packaging 108 has expired, that the patient complied with the instructions, or that the medication packaging 108 has or has not been tampered with. In order to determine the condition of the packaging, the processor 102 and/or the communications device 106 can include a device/reader capable of retrieving the medication information from the adjustable machine-readable medium. For example, a barcode scanner can be utilized to read an adjustable barcode contained on the medication packaging 108.

Instead of or in addition to utilizing a reader to retrieve the information from the machine-readable medium, the communications device 106 can capture and store an image (such as through photographing) of the machine-readable medium. The communications device 106 can then automatically read the medication information from the image of the machine-readable medium. The machine-readable medium can be read and the medication information can be stored and managed by the processor 102 and/or the communications device. Notably, the medication information can be forwarded to the processor 102 by the communications device 106.

According to one embodiment, the processor 102 and/or the communications device 106 can be configured to determine if the medication packaging 108 is in an unused state. An unused state can occur when the machine-readable medium has not been adjusted. For example, if the patient did not take the medication as instructed and did not tamper with the medication packaging 108, the machine-readable medium would not be adjusted because no medication was dispensed. When the machine-readable medium is read, the unadjusted machine-readable medium would indicate that the medication packaging 108 was unused.

In another embodiment, the processor 102 and/or the communications device 106 can be configured to determine if the medication has been dispensed from the medication packaging 108. The medication can be indicated as being dispensed if a portion of the machine-readable medium has been adjusted. The portion of the barcode to be adjusted can correspond to the medication. For example, if the patient dispensed the medication from the medication packaging 108, then a portion of a barcode would be adjusted to reflect the fact that the medication was dispensed. After reading the adjusted barcode, the communications device 106 can determine that the medication was indeed dispensed. In yet another embodiment, the processor 102 and/or communications device 106 can be configured to acknowledge/verify that the medication was dispensed from the medication packaging 108. As an illustration, the communications device 106 can display "Medication X has been dispensed" to the patient after reading an adjusted machine-readable medium. In still another embodiment, the processor 102 and/or communications device can provide a reward to the patient for having successfully taken/dispensed their medication. For example, the communications device 106 can retrieve and display a digital gift certificate, coupon, or other reward to the patient after verifying that the medication dispensed.

Figure 2:
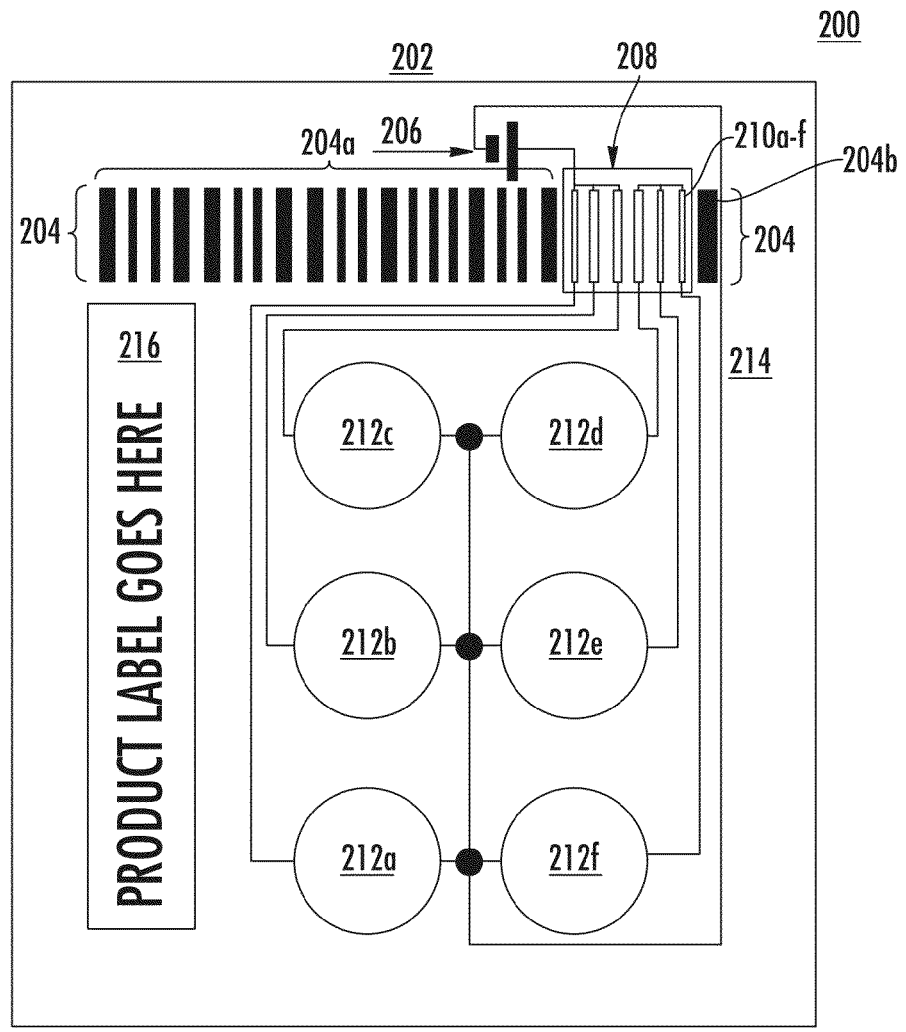
FIG. 2 is a schematic view illustrating a medication packaging including an adjustable barcode according to the invention.

Referring now also to FIG. 2, a schematic view illustrating a medication packaging 200 including an adjustable barcode according to the invention is shown. Notably, the medication packaging 200 can be utilized in the system 100. The medication packaging can include a card 202 having a top and bottom surface. Notably, the card 202 can be made of cardboard or other materials. The medication packaging 200 can also include a machine-readable medium, such as barcode 204, an optical disk, a magnetic disk, a readable card, a readable tape, a magnetic strip, a radio frequency tag, and/or other machine-readable mediums. The barcode 204 can include a barcode preamble 204a, which can describe, but is not limited to describing, the medication contained in the medication packaging 200 in a manner that is consistent with the package labeling 216. Additionally, the barcode can include a printed stop bit 204b or other character, which can indicate the end of the barcode sequence.

In an embodiment; the medication packaging 200 can also include a power source 206, a swatch of thermal sensitive paper 208, an array of resistive strips 210a-f (the farthest left resistive strip being 210a), and a series of object/medication holders 212a-f. In this case, the power source 206 can be a battery. The thermal sensitive paper 208 can reside over the array of resistive strips 210a-f, which can reside adjacent to a portion of the barcode 204. In FIG. 2 the thermal sensitive paper 208 is between the preamble 204a and the stop bit 204b. The series of object holders 212a-f can be a blister-pack technology for containing a number of medications, which can be in pill and/or liquid form. Notably, the power source 206 can be operably coupled to the array of resistive strips 210a-f, the barcode 204, and the object holders 212a-f via wires 214. The barcode 204 can be adjustable upon dispensing an object from an object holder of the object holders 212a-f.

Figure 3A:
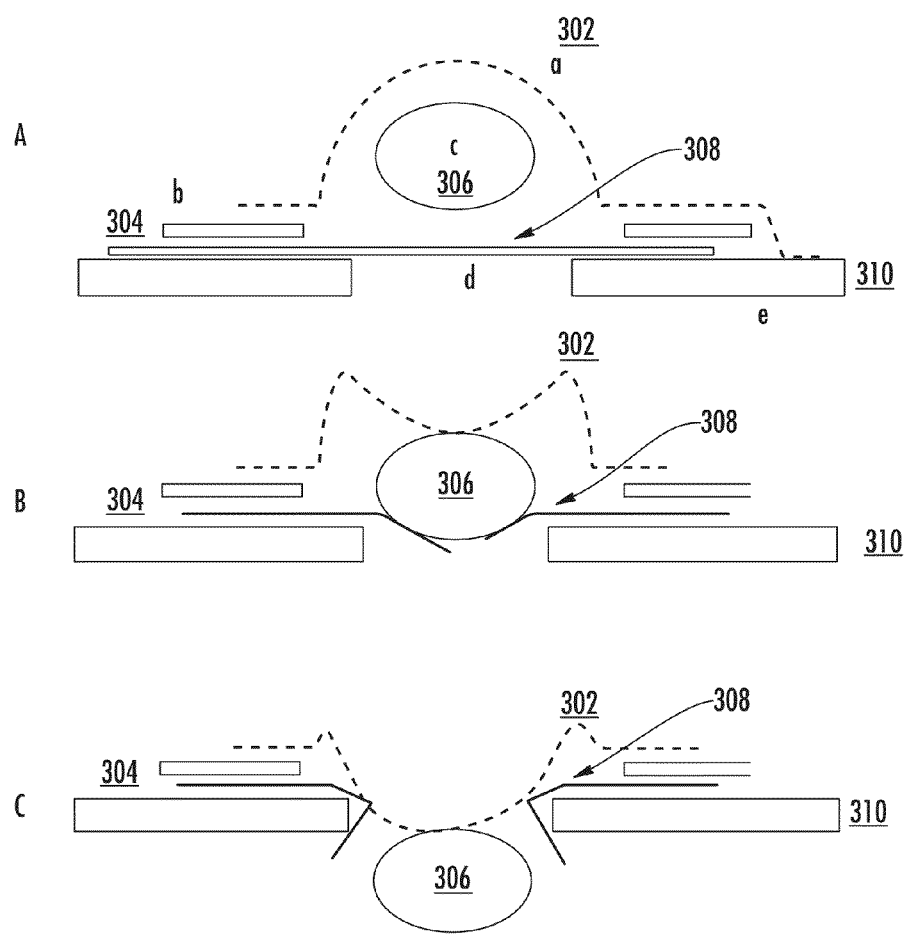
FIG. 3A is an illustration depicting a side view of a dispensing sensor, which can be included in a medication packaging.
Figure 3B:
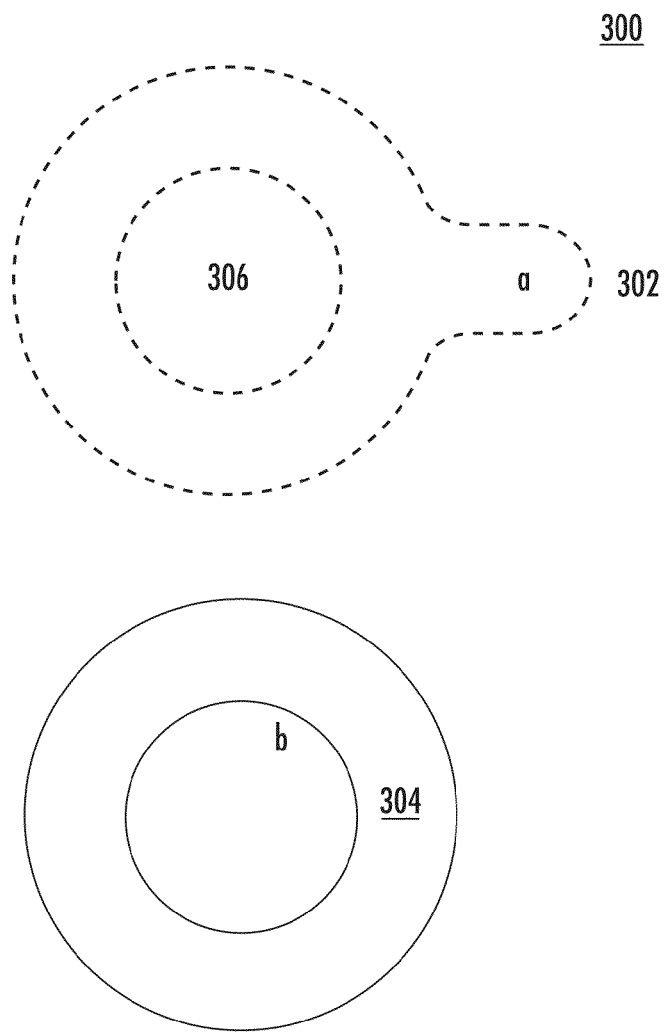
FIG. 3B is an illustration depicting a top view of the dispensing sensor.

Referring now also to FIG. 3A, a side view of an object holder/dispensing sensor 300 undergoing various states (A), (B), and (C) is illustratively shown. In an embodiment, each object holder 212a-f can serve as a specialized contact switch and can comprise a conductive cover 302, an insulator 304, and a conductive foil 308. The object holders 212a-f can include a medication 306 and can reside on a card 310. The conductive foil 308 can be embossed with preferential patterns for tearing. Referring now also to FIG. 3B, a top view of the object holder/dispensing sensor 300 is shown, which shows the conductive cover 302 and the medication 306 separately from the insulator 304. Referring back to FIG. 3A, state (A) illustrates the object holder 300 in a normal state with the medication 306 contained within the object holder 300.

According to another embodiment, the conductive cover 308 can be depressed, which can cause the conductive foil 308 to tear and release the object/medication 306 from the object holder 300 via the hole in the card 310. State (B) illustrates the conductive cover 302 being depressed and the tearing of the conductive foil 308. In another embodiment, the conductive cover 302 can contact the conductive foil 308 (state (C)), thereby closing a circuit with the power source 206 to at least one resistive strip of the array of resistive strips 210a-f. This can cause the resistive strips 210a-f to rapidly heat and self destruct, wherein the heating and destruction process can cause the thermal sensitive paper 208 to create a readable image on the thermal sensitive paper 208. The effect of creating the readable image, for example, is to create a bar or to extend a bar, such that at least one "bit" of the full barcode 204 is altered. This effectively adjusts the barcode 204, which can now indicate which medication 306 was dispensed. As an illustration, if the conductive cover 302 for object holder 212a contacts the conductive foil 308, the resulting closed circuit can cause resistive strip 210a to self-destruct, thereby creating a readable bar corresponding to object holder 212a on the thermal sensitive paper 208. The adjusted barcode 204 can be read by a device configured to read the barcode 204 and the medication information corresponding to the adjusted barcode 204 can be stored. In one embodiment, the adjustable barcode 204 can be utilized to indicate when the power source 206 expires.

Figure 4:
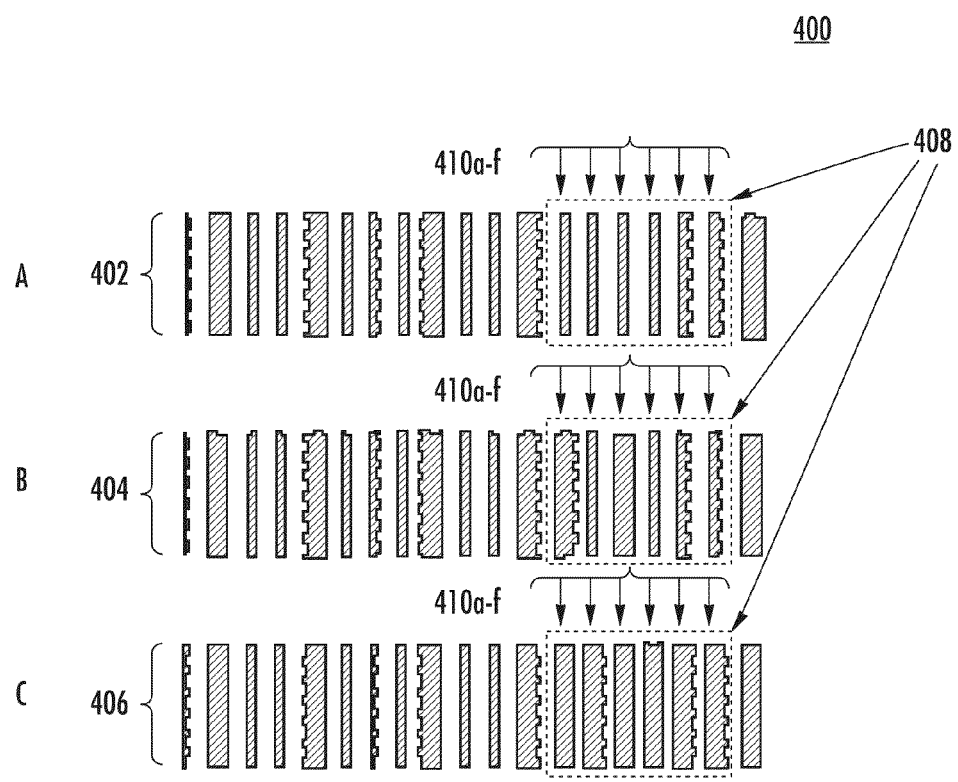
FIG. 4 is an illustration depicting various states of an adjustable barcode.

Referring now also to FIG. 4, an illustration depicting various states of an adjustable barcode 400 is shown. State (A) 402 illustrates the adjustable barcode 400 in a state where none of the "bits" 410a-f on the thermal paper 408 have been widened. This can indicate that the medication packaging featuring this state is either new or unused. State (B) 404 illustrates two "bits" 410a and 410c that have been widened on the thermal paper 408. Notably, the location of "bits" 410a and 410c can correspond to the location of resistive strips 210a and 210c from FIG. 2. Since the two "bits" 410a and 410c have been widened, this can indicate that medicine has been dispensed from object holders 212a and 212c, that the medications were taken out of sequence, and/or that one or more medications were not taken according to the required regimen. State (C) 406 illustrates the adjustable barcode 400 in a state where all object holders 212a-f have been dispensed, which can indicate an empty or tampered medication package.

Figure 5:
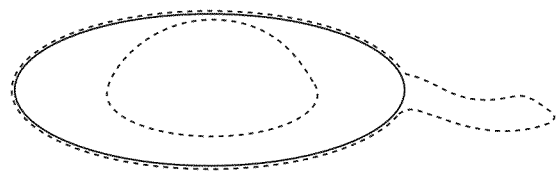
FIG. 5 is an illustration depicting a tear-away tab for use in medication monitoring.
Figure 5:
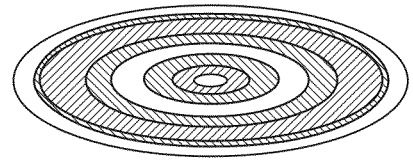

According to another embodiment, the medication packaging 200 can include a tear-away structure for providing monitoring of medication compliance. The tear-away structure does not have to be electrical in nature. Referring now also to FIG. 5, an illustration depicting an object holder 500 including a tear-away tab 502 is shown. The tear-away tab 502 can be torn from a medication packaging to reveal an alternate color, shade, or pattern 504. This alternate color or pattern can serve as an indication to the patient that the medication corresponding to that particular spot on the medication packaging was dispensed. In another embodiment, when the tear-away tab 502 is torn off the medication packaging, it can reveal an alternate barcode, which can be read by a communications device or processor. The alternate barcode can provide dispensing information or other information.

Figure 6A:
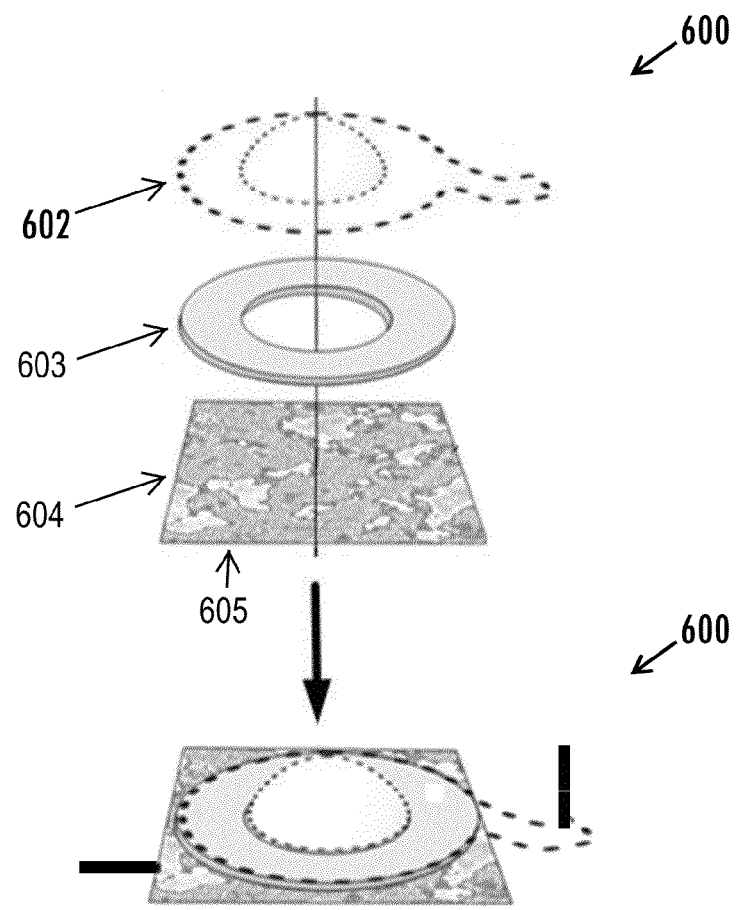
FIG. 6A is a schematic view illustrating an exploded perspective partially in phantom of the different components of a medication package, according to an embodiment of the invention.
Figure 6B:
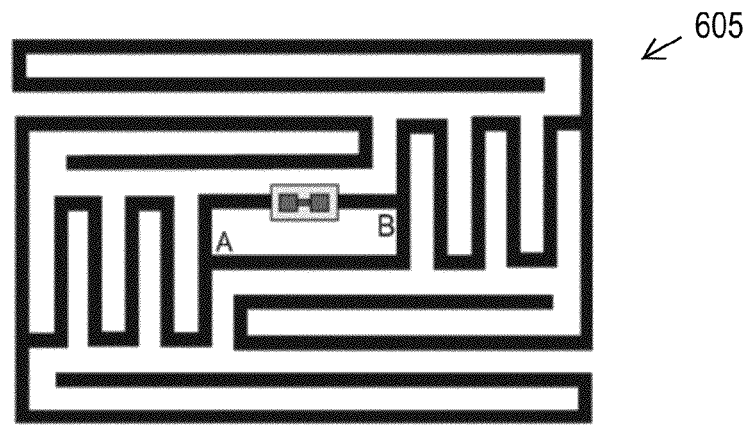
FIG. 6B is an illustration of a radio frequency identification device RFID device utilized with a medication package, according to an embodiment of the invention.

In another embodiment of the invention, referring to FIG. 6A, a schematic view of an exploded perspective partially in phantom of the different components of a medication package 600 is shown. The different components can include a conductive cover 602, insulator 603, and conductive foil 604. An RFID device 605 shown in FIG. 6B can be provided with the medication package 600 such that removal of the medication can activate the RFID 605. The electrical contact created when the conducting cover 602 contacts the conductive foil 604 can be utilized to activate the RFID device 605. The RFID 605 can be applied to the conductive foil 604 such that tearing of the conductive foil 604 can indicate that the medication has been dispensed or that the packaging has been tampered with. The RFID device 605 is typically a passive resonant circuit, which can re-radiate with an active component powered by received energy. However, some RFID devices are active and contain their own power source. Instead of an RFID device 605, a Bluetooth interface, or other remote connectivity means can be utilized. By either covering an antenna pattern over the tear-away portion of the medication package 600, changing resonance (by opening points A and B of the RFID 605 illustrated in FIG. 6B), or by direct input to the active component to modulate and enable transmission, one can indicate that a medication has been dispensed or that the packaging has been tampered with, as removal exposes or modifies an RFID circuit. Additionally, RFID energy can be utilized for augmenting or replacing the power source 206 and/or to modify the barcode 204 mentioned in FIG. 2 for inventory purposes or preventing the sale of expired or tampered products.

Figure 7:
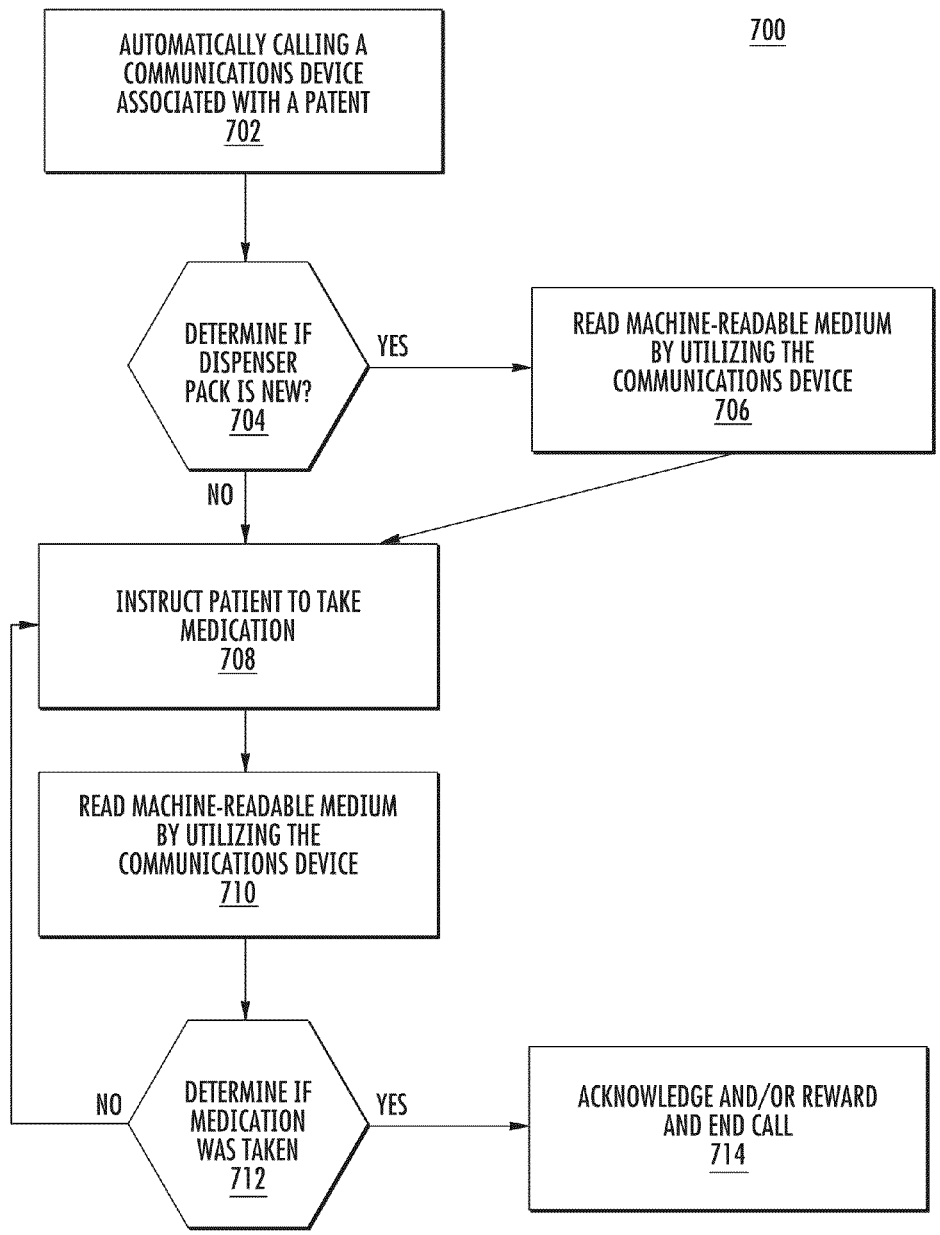
FIG. 7 is a flowchart of steps for monitoring and verifying medication compliance, according to a particular embodiment of the invention.

Referring now to FIG. 7, a flowchart of steps of method 700 for monitoring and verifying medication compliance in according with the system 100 is illustrated. The method 700 can include, at the start step 702, automatically calling the communications device 106 associated with patient by utilizing the processor 102. Also, the method can include determining if the medication packaging/dispenser pack is new at step 704. If the answer is yes, then the machine-readable medium can be read by communications device 106 at step 706. From here, the patient can be instructed to take medication at step 708. If the answer was no, the method 700 can proceed to instructing the user to take the medication without having to necessarily read the machine-readable medium.

Once the patient has been instructed to take the medication, the machine-readable medium can be read by utilizing the communications device 106 at step 710. It can then be determined whether the medication was dispensed or taken at step 712. If the medication was not dispensed or taken then the method can revert to step 708 and instruct the patient again. If the medication was dispensed, then the patient can receive an acknowledgement/verification, receive a reward, or have the call terminated at step 714.

Figure 8:
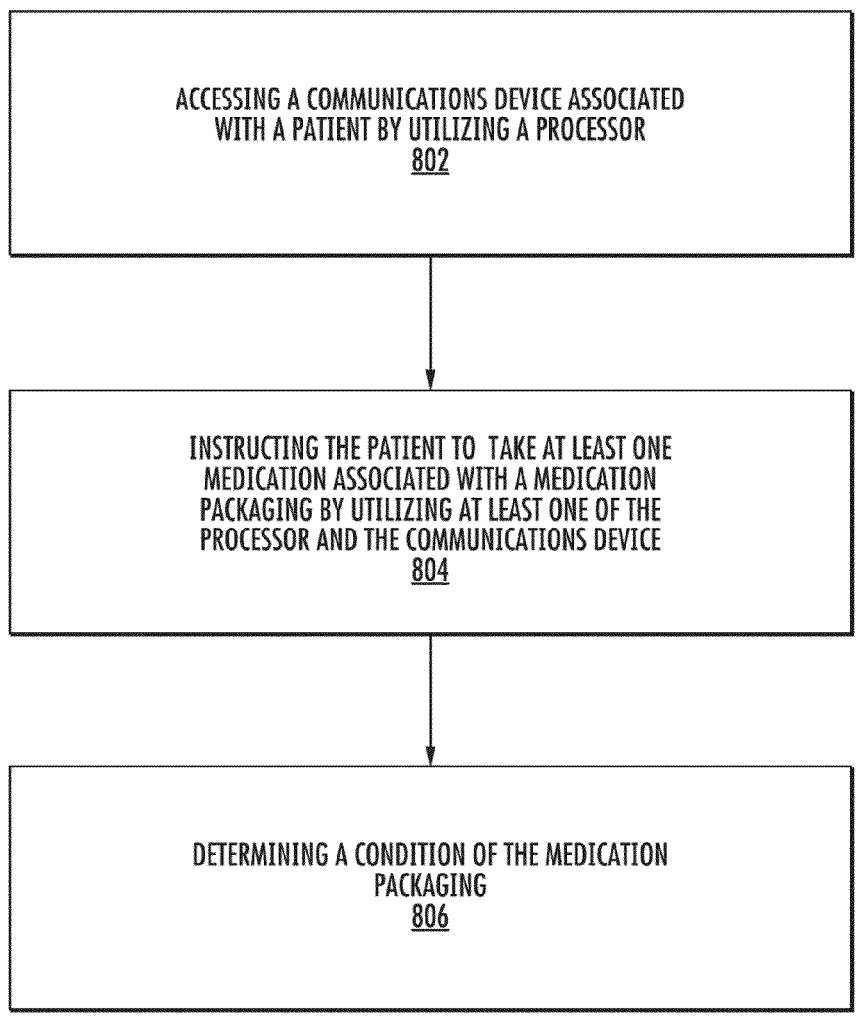
FIG. 8 is a flowchart of steps in a method for monitoring medication compliance, according to another embodiment of the invention.

Referring now to FIG. 8, a flowchart is provided that illustrates certain method aspects of the invention. The flowchart depicts steps of a method 800 for monitoring medication compliance. The method 800 illustratively can include, beginning at step 802, accessing a communications device associated with a patient by utilizing a processor. The method 800 can also include instructing the patient to take one or more medications associated with a medication packaging by utilizing one or more of the processor and the communications device at step 804. Furthermore, the method 800 can include determining a condition of the medication packaging at the concluding step 806.

According to a particular embodiment of the method 800, either the processor, the communications device, or both the processor and communications device can be configured to store, receive, and maintain medication information and/or information relating to the patient. In one embodiment, the condition of the medication packaging can indicate a dispensing of a medication of the one or more medications from the medication packaging, whether the one or more medications from the medication packaging has expired, and whether the medication packaging has been tampered with. In another embodiment, the method 800 can include acknowledging that a medication of the one or more medications was dispensed from the medication packaging. For example, the communications device can display an acknowledgment stating that the patient effectively dispensed the medication. The acknowledgement can also include notifying the patient through other means, such as through sound, printing out a confirmation, and the like.

The method 800 can also include rewarding the patient for having taken the medication or having dispensed the medication from the medication packaging. For example, the reward could be in the form a of a coupon, which can be displayed on or printed from the processor or communications device and can be utilized to reduce the price of a future medication purchase. The method 800 can further include terminating access to the communications device after the determining step.

According to an embodiment, the medication packaging can comprise a machine-readable medium. The machine-readable medium can be a barcode, optical disk, magnetic disk, card, tape, magnetic strip, radio frequency tag, or other machine-readable medium. Notably, the machine-readable medium can comprise medication information and other information. For example, if the machine-readable medium is a barcode, the barcode can describe the medication in a manner that is consistent with the labeling on the package itself. In another embodiment, the machine-readable medium and corresponding medication information can be adjustable based on the dispensing of the medication from the medication packaging. For example, upon dispensing the medication from the packaging, the barcode can be altered or widened in such a way so as to indicate that the medication effectively dispensed.

In one embodiment, the method 800 can further include retrieving the medication information of the adjustable machine-readable medium by utilizing the communications device. For example, the communications device can have a built-in barcode reader to read the medication information from the adjusted or unadjusted machine-readable medium. Also, the communications device can also photograph and take an image of the adjusted or unadjusted machine-readable medium. Using the photograph, the communications device or the processor can read the information from the image.

In another embodiment, the method 800 can include determining if the medication packaging is in an unused state based on the retrieving step. The medication packaging can be in an unused state if the machine-readable medium has not been adjusted. As an illustration, if no medication has been dispensed, then the barcode would not be widened or altered. When the built-in reader reads the unadjusted barcode, it would indicate that the medication packaging had not been used by the patient. In yet another embodiment, the method 800 can include determining if a medication had been dispensed from the medication packaging, wherein the determination can be based on the retrieving step. In this case, the medication can be indicated as having been dispensed if a portion of the machine-readable medium corresponding to the one or more medications has been adjusted. In still another embodiment, the method 800 can include instructing the patient again to take the one or more medications if it is determined that the one or more medications has not been dispensed. It is important to note that the method 800 can incorporate aspects of other embodiments of the invention illustrated herein, such as those incorporated in the system 100.

In operation, a health care provider, such as a pharmacist with a barcode reader could scan a machine readable indicator on the medication package, such as a barcode on a blister pack. Alternatively, an image of the medication package can be captured by a camera in a mobile communications device. Additionally, a patient having access to a barcode reader could scan the barcode or position the medication package to a cell phone camera and the barcode can be deciphered by the system or a medical web service. In another operation of the present invention, a pen type bar code reader coupled with a cell phone device can be used to process the barcode of medication dosage compliance. Prescription errors and lack of patient compliance are important factors in medical errors and improper recovery. Benefits of the present invention include a legal digital record of compliance that indicates to both patients and health care providers that the correct medicine was taken at the correct time.

In another embodiment, a method for medication compliance can include supplying to a patient a medication package including a machine readable indicator of medication dosage compliance. The machine readable indicator can generate medication compliance information associated with the patient. For example, the machine readable indicator can be a barcode, optical disk, magnetic disk, card, tape, magnetic strip, radio frequency tag, or other machine-readable medium. The machine readable indicator can include medication compliance information. The method can also include providing a communications device capable of accessing and obtaining the medication compliance information from the medication package. Finally, the method can include sending the obtained medication compliance information to a processor for managing medication compliance information associated with the patient. Alternatively, the processor can be configured to interpret the machine readable indicator, such as a barcode. Responsive to determining that a patient has complied with properly taking medication, either the health care provider or the processor can send the patient a positive message confirming proper compliance by the patient.

In yet another embodiment, a medication compliance monitoring system or device can be provided. The system can include a medication package having at least one compartment which is yieldable for medication removal, such as a blister pack. The system can also include a machine readable indicator including medication compliance information, disposed on the medication package such that removal of a unit dose of medication from each compartment will cause a transformation of the machine readable indicator. The transformation can include the medication compliance information associated with the patient being updated based on the transformation of the machine readable indicator. The system can also include a communications device configured for obtaining the medication compliance information from the medication package. Furthermore, a processor can be configured for receiving the obtained medication compliance information from the communications device for managing medication compliance information associated with the patient. The processor can be communicatively linked to a storage medium, such as memory and can include program code enabled to supply to a patient a medication package including a machine readable indicator of medication dosage compliance, the indicator generating medication compliance information associated with the patient. Program code enabled to provide a communications device capable of accessing and obtaining the medication compliance information from the medication package can be provided. Additionally, sending the obtained medication compliance information to the processor for managing medication compliance information associated with the patient can be included in the program code.

Although the various embodiments have been described above generally with respect to medication products and packaging, the various embodiments are not limited in this regard. Rather, the packaging techniques described above are equally applicable to packaging of other types of products. For example, the various methods described above for altering bar codes and other labeling are equally suitable for providing labels that can be used to indicate or determine the value, usage, and suitability for sale or use of other types of products.

First, packaging in accordance with the various embodiments can be utilized to determine value of the product packaged therein. For example, because a unique universal product code (UPC) or specifying label is required to define a particular brand and size of canned soft drink, that product always sells as a specific commodity and sellers are typically limited to a single price for the product, regardless of its state. However, in many cases, the state of a product can make more or less valuable to buyers.

Therefore, the various embodiments allow a seller to vary the value of the product at time of sale based on its state. That is, in some embodiments, a Value Dependent Product Code (VDPC) is provided. For example, a refrigerated can or bottle of soda, beer, or wine might be of higher value to buyers than their unrefrigerated counterparts. However, the common UPC label for such products results in a same price for the product, regardless of its refrigeration state. Accordingly, a UPC label can be configured, in accordance with the various embodiments to change in response to temperature, such as via a sensor, which causes an alternate UPC label to be presented when the product is refrigerated. As a result, such labels in accordance with the various embodiments enable the buyer to price the refrigerated and unrefrigerated products differently, and recoup the added value provided by their refrigeration. Such alternate labeling is not limited to refrigerated products, and can be equally applied to products that have added value after heating.

Second, packaging in accordance with the various embodiments can be utilized to determine suitability of the product packaged therein. Referring back to the soda can example above, if the can were to freeze and its contents expand, the packaging might not necessarily be sealed. Accordingly, the product might be precluded from sale until inspected. The can might also be precluded from sale if it had lost pressure or if exposed to high heat sometime in distribution, thereby altering the chemical composition of artificial sweeteners for example. Accordingly, the UPC label can also be configured to respond to such event.

Third, packaging in accordance with the various embodiments can be utilized to determine usage or handling. Referring back to the soda can example, if the can had been "shopworn", that is, dropped, excessively handled and moved around, or has past or is approaching its expiration date, such products may be of lesser or no value to buyers. As a result, sellers are normally forced to dispose of shopworn products, unable to recoup their costs for obtaining them. Of even greater concern is that shopworn products may not be detected and yet are sold, possibly harming the buyer. Accordingly, the various embodiments of the invention can also be configured to provide alternate labeling in response to products being shopworn. Thus, the seller can adjust pricing for shopworn products or intercept them prior to the buyer completing the purchase.

In the scenarios described above, the label change may be indelible or vary in real time, or show environmental conditions as a history.

In some embodiments, the varying label can be used to provide an interactive experience for buyers. For example, the packaging can include a label that changes if the product is installed, activated, or authenticated to be genuine before purchase. In other embodiments, the label might be changed at time of sale to indicate the beginning of a warranty.

In yet other embodiments, the seller can generate signals that cause the changes to a label to reflect changes in values, suitability, or usage. In other words, instead of relying on sensors or the like in the packaging, the information regarding the change in state or the occurrence of an event is transmitted or otherwise communicated to the packaging in order to cause the change in the label. However, in still other embodiments, a combination of signals from sensors and externally generated signals can be used.

In still other embodiments, the labels can be used by sellers to determine pricing for specific customers. For example, in the case of tires, a label on a car's existing tires can be configured, as described above, to relate the usage and status of the tires and adjust pricing of replacements automatically, based on the need to replace the tires. That is, if the label information can be used with a shop's system to automatically the replacement tires based on the treadwear indicated by the label. Thus, if a large amount of treadwear is left, the shop's system can be configured to automatically discount the tires, based on the amount of treadwear, to entice the buyer to purchase replacements. Thus, as less treadwear is left, a smaller discount is applied.

In addition to the embodiments described above, the various embodiments can be used to provide other types of pricing or purchasing features. For example, a label can change pricing by the quantity of items in the package such that an initial label might apply to the package including all the items and that is automatically reduced as items are added or removed.

The bar code may not necessarily be read at time of sale—it may be read on inventory, or as pass/fail for sales, or interactively.

In another embodiment, for the purposes of reducing dependence on sales clerks in stores, the label can be altered after a buyer makes an unassisted purchase. For example, over a smart phone or other computing device associated with the user, the user could pre-purchase the item and the item's label is automatically altered. Accordingly, when the buyer picks up the item, the label can indicate that buyer has already paid for the item. Thus, the store's security system is disabled for that one item. Additionally, this allows an item to be automatically reserved. That is, the label can indicate that no other buyers may purchase or leave the store with the one item.

Although various exemplary embodiments have been described above, these are provided solely as examples and the various embodiments are not limited in this regard. For example, other embodiments of the invention include: a diabetes or other medical test, whose bar code changes to indicate the outcome; a package of batteries, who code changes as they near end of shelf life; a radiation dosimeter that changes a visually or machine readable label if the person wearing it has been over exposed; or a passport with an embedded GPS system that shows where the traveler has actually traveled (for purposes of homeland security). Various other embodiments are possible.

The invention can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, (defining a computer program) which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding description of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A computer-based system for monitoring packaged products, the system comprising:
   at least one processor configured to process and manage data;
   at least one communications device communicatively linked to the at least one processor; and
   at least one packaging for one or more products, the packaging comprising a machine-readable medium, wherein the machine-readable medium comprises product information;
   wherein the at least one processor is configured to receive the product information of the machine-readable medium, wherein the machine-readable medium and corresponding product information are adjustable based on at least one of a current or a past state of the at least one packaging, wherein the at least one communications device captures and stores an image of the machine-readable medium, and wherein the at least one communications device retrieves the product information from the image.

2. The system of claim 1, wherein the at least one communications device is configured to forward the product information to the at least one processor.

3. The system of claim 1, wherein the at least one communications device comprises a reader configured to retrieve the product information from the adjustable machine-readable medium.

4. The system of claim 1, wherein at least one of the at least one processor and the at least one communications device is configured to determine if the at least one packaging is in an unused state, wherein the at least one packaging is in an unused state if the machine-readable medium has not been adjusted.

5. The system of claim 1, wherein at least one of the at least one processor and the at least one communications device is configured to determine if the products from the at least one packaging have been accessed, wherein the products has been accessed if a portion of the machine-readable medium corresponding to the products has been adjusted.

6. The system of claim 1, wherein at least one of the at least one processor and the at least one communications device is configured to perform at least one of acknowledging that the products from the at least one medication packaging were accessed and providing a reward.

7. The system of claim 1, wherein the machine-readable medium is at least one of a barcode, optical disk, magnetic disk, card, tape, magnetic strip, radio frequency tag, and other machine-readable medium.

8. A packaging for one or more products, the packaging comprising:
   at least one product holder; and
   a machine-readable medium operably coupled to the at least one product holder, wherein the machine-readable medium is adjustable upon at least one of removal of product from the at least one product holder, a current state of the product holder, or a past state of the product holder, wherein the machine readable medium is a barcode disposed on a thermal sensitive paper, wherein the thermal sensitive paper resides over an array of resistive strips residing adjacent to a portion of the barcode.

9. The packaging of claim 8, further comprising a power source operably coupled to the array of resistive strips and to the at least one product holder, wherein upon closing a circuit between at least one resistive strip of the array of resistive strips and power source, causes the at least one resistive strip to heat, thereby causing the at least one resistive strip to alter the thermal sensitive paper to create a readable image on the thermal sensitive paper to alter the barcode.

10. The packaging of claim 9, wherein the at least one object holder comprises a sensor, and wherein the sensor, upon a signal from the sensor meeting a criteria, causes the circuit between the power source and the array of resistive strips to be closed.

11. The packaging of claim 10, wherein the signal is activated by at least one of a radio frequency device, Bluetooth interface, and other remote connectivity means.

12. The packaging of claim 9, wherein the at least one object holder comprises a conductive cover, an insulator, and a conductive foil, and wherein the conductive cover, upon being depressed, causes the conductive foil to tear and release the object from the at least one object holder.

13. The packaging of claim 12, wherein the conductive cover contacts the conductive foil thereby closing a circuit with the power source.

14. A packaging for one or more products, the packaging comprising:
   at least one product holder for holding at least one product; and
   a label operably coupled to the at least one product holder, wherein the label comprises at least one set of indicia defining a machine-readable medium, wherein the at least one set of indicia is visible after the coupling of the label to the at least one product holder, and wherein the at least one set of visible indicia is adjustable based on at least one of an automated signal or an interactive signal.

15. The packaging of claim 14, further comprising at least one sensor for generating the automated signal, the sensor generating the automated signal based on at least one of a status of the at least one product or the at least one product holder.

16. The packaging of claim 15, wherein the at least one sensor comprises at least one of a temperature sensor, a pressure sensor, or tamper sensor.

17. The packaging of claim 15, wherein the status is based on a current state of the at least one product or the at least one product holder.

18. The packaging of claim 15, wherein the status is based on a history of states of the at least one product or the at least one product holder.

19. The packaging of claim 14, further comprising at least one sensor for generating the interactive signal, the sensor generating the interactive signal based on at least one of a status of the at least one product or the at least one product holder and an remotely generated signal.

20. The packaging of claim 19, wherein the sensor further comprises at least one transceiving device for receiving the remotely generated signal.

21. The packaging of claim 14, wherein the adjusting of the label is permanent.

22. The packaging of claim 14, wherein the machine readable medium is a barcode.

23. The packaging of claim 22, wherein the machine readable medium further comprises an array of resistive strips and a thermally sensitive material having the barcode disposed thereon, the packaging further comprising a power source operably coupled to the array of resistive strips and to the at least one product holder, wherein upon closing a circuit between at least one resistive strip of the array of resistive strips and power source, causes the at least one resistive strip to heat, thereby causing the at least one resistive strip to alter the thermal sensitive paper to alter the barcode.

24. The packaging of claim 14, wherein the label is not a human readable medium.

\* \* \* \* \*